United States Patent [19]

Worden et al.

[11] Patent Number: 5,228,514
[45] Date of Patent: Jul. 20, 1993

[54] GAS TRAP APPARATUS

[75] Inventors: Raymond D. Worden, Houston; Lawrence R. Kubecka, Wharton, both of Tex.

[73] Assignee: Ruska Laboratories, Inc., Houston, Tex.

[21] Appl. No.: 978,640

[22] Filed: Nov. 19, 1992

[51] Int. Cl.⁵ ............................................. F25B 29/00
[52] U.S. Cl. ..................................... 165/155; 165/154; 165/135; 165/64; 165/61
[58] Field of Search .................... 165/61, 64, 133, 135, 165/154, 155

[56] References Cited

U.S. PATENT DOCUMENTS

| | | | |
|---|---|---|---|
| 3,334,686 | 8/1967 | Barrett | 165/155 |
| 3,525,928 | 8/1970 | Nagao et al. | 165/155 X |
| 4,242,001 | 12/1980 | Meintker et al. | 165/155 X |
| 4,671,351 | 6/1987 | Rappe | 165/155 X |
| 4,986,343 | 1/1991 | Sing | 165/135 X |
| 5,033,541 | 7/1991 | D'Silva | 165/155 |

Primary Examiner—John Rivell
Attorney, Agent, or Firm—Browning, Bushman, Anderson & Brookhart

[57] ABSTRACT

A gas trap apparatus is disclosed for trapping gaseous fraction of mixtures. The apparatus includes a gas column chamber into which a tubular column, such as a capillary tube, may extend. A cooling chamber is provided into which a coolant may be introduced for solidifying or liquefying a gas sample. A heating element in surrounding relationship to the cooling chamber is used for vaporizing the solidified/liquified gas. A Dewar flask surrounds the gas trap apparatus to prevent thermal leakage to the atmosphere.

9 Claims, 1 Drawing Sheet

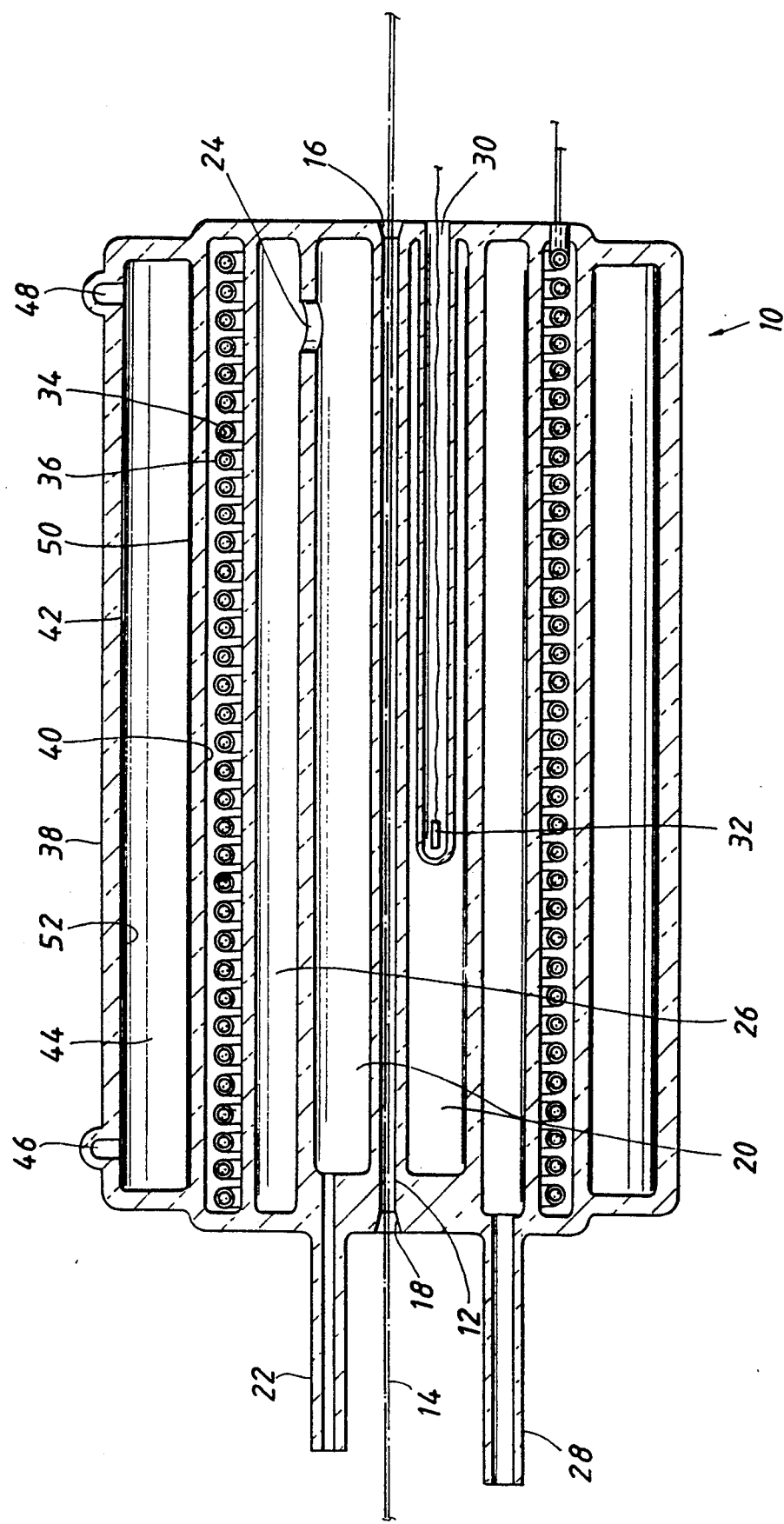

GAS TRAP APPARATUS

FIELD OF THE INVENTION

The present invention relates to an apparatus for trapping gaseous fractions of mixtures. More particularly, the present invention relates to a gas trap with a coolant chamber for transforming gaseous samples to solids or liquids.

BACKGROUND OF THE INVENTION

There are numerous instances in the analysis of complex mixtures where it is desirable, indeed even necessary, to isolate and determine the structure of various individual components of the mixture. For example, in pyrolytic analysis or thermal extraction techniques, materials such as polymers and other organic and inorganic solids are subjected to high temperatures to thermally degrade and/or effect separation of components of the material. It will be appreciated that in such techniques, a myriad of various products may be produced or evolved. In order for these analysis techniques to be meaningful, it is necessary that the evolved products be identified so that conclusions can be reached regarding the structure of the sample subjected to analysis, the mechanism of decomposition, etc. An emerging use of pyrolytic analysis or thermal extraction techniques is in the environmental field where it is frequently necessary to subject solid samples to analysis to determine contaminating constituents. For example, soil samples contaminated with organic materials that may be toxic can be subjected to thermal extraction to thermal separate the organic components from the soil. Clearly, identification of the evolved components is of the utmost importance.

It is common practice in the field of instrumental analysis, e.g., gas chromatography, mass spectrometry, etc. to separate a complex mixture of compounds into individual components by passing the components through a chromatographic column using a carrier or sweep gas. Typically, although not always, the chromatographic column will contain a substrate the exhibits different affinities for the individual components. Accordingly, as the individual components are carried through the column by the carrier gas, they are more or less retained or held up by the substrate depending upon their affinity for the substrate with the net result that the components are separated and elute, ideally individually, from the column.

One problem in the separation of components is that very light, normally gaseous components, e.g., $C_1$–$C_4$ hydrocarbons, produced as a result of thermal extraction and/or pyrolytic analysis, do not evolve as a single peak from the sample being analyzed. Consequently, as they are evolved in the thermal extraction technique, they tend to be swept through the separating column without much separation with the result that no discernible peak is observed. Accordingly, it is not possible to identify these highly volatile components.

To solve this problem, it is known to trap the lower boiling components prior to their entering the separation or chromatographic column so that instead of slowly bleeding through the chromatographic column, the entire trapped sample can be injected, virtually instantaneously, into the column so that separation of the individual components of the low boiling mixture can be achieved, each component giving a well-defined peak. To accomplish this, it is necessary to have a trapping apparatus that can be rapidly converted from a high temperature to a very low temperature and then back to a high temperature again.

For example, a trap can consist of a section of tubing through which the carrier gas containing the components flows, the section of the tubing being immersed in liquid nitrogen or some other such cooling medium that will effectively solidify (freeze) the components and cause them to be removed from the carrier gas. It must be remembered that, typically, the carrier gas and the components therein are at elevated temperatures to prevent certain components from condensing out in the column. Once components have been trapped, it is then necessary to revaporize them so that they can be removed from the trap and directed into the chromatographic column for separation. It is also desirable for speed of analysis that it be possible to rapidly raise the temperature of the trapped (frozen) components so that they can be vaporized from the trap rapidly.

Prior art traps of the type described above are generally cumbersome, multipart devices that do not readily lend themselves to easy trapping of a sample by freezing and then rapid vaporization of the trapped sample when desired.

SUMMARY OF THE INVENTION

It is therefore an object of the present invention to provide a gas trap for removing components from a gaseous stream.

A further object of the present invention is to provide a gas trap that can revaporize trapped gaseous components.

Another object of the present invention is to provide means for trapping components in a gas stream in a capillary tube that extends through the gas trap.

The apparatus of the present invention includes a gas column chamber means into which extends at least a portion of a tubular column which may be a capillary tube. A means for introducing a coolant into an annulus in surrounding relationship to said gas column chamber is operational for liquefying/solidifying the gas sample. The apparatus also includes a heating means for heating the gas column chamber. The heating means is in surrounding relationship to the coolant annulus.

The above and other objects of the present invention will become apparent from the drawing, the description herein and the amended claims.

BRIEF DESCRIPTION OF THE DRAWING

FIG. 1 is a side elevational view, partially in section, showing a gas trap apparatus in accord with the present invention.

DETAILED DESCRIPTION OF THE PREFERRED EMBODIMENT

The present invention provides a means for trapping a gas sample to be analyzed. For this purpose, the gas sample is cooled to a liquid/solid state within the gas trap of the present invention. The present invention also includes means for heating the liquified/solidified gas, as required, to vaporize the gas sample.

The main internal components of gas trap 10 of the present invention are shown in FIG. 1. The gas sample typically flows through gas tubular column 14. Generally, tubular column 14, which may be capillary tube, will extend through gas column chamber 12 entering at end 16 and exiting at end 18. Ends 16 and 18 may be funnel-shaped to thereby allow easy threading of tubular column 14 through gas column chamber 12. Installation of the trap to the available configuration is thus readily accomplished. Ends 16 and 18 may include connections (not shown) for connecting both sides of gas trap 10 to respective capillary tubes if desirable. If desired, an installation could have tubular column 14 terminating with gas column chamber 12.

In surrounding relationship to gas column chamber 12, is coolant chamber 20. In a preferred embodiment, liquid nitrogen flows through coolant input port 22 to fill coolant chamber 20. Other coolants besides liquid nitrogen also could be used with the present invention. Liquid nitrogen provides a cooling temperature of approximately −200° C. for liquefying the sample gas in gas column chamber 12. Other means for cooling the annulus around gas column chamber 12 may also be used such as cooling coils (not shown). Coolant could be pumped through cooling coils encircling gas column 12.

Coolant exits coolant chamber 20 through port 24 to coolant exhaust chamber 26. Coolant exhaust chamber 26 is an annular chamber or tubular chamber in surrounding relationship to coolant chamber 20. The coolant that exits coolant chamber 20 is in a gaseous and/or liquified state. Coolant exits coolant exhaust chamber 26 through coolant output port 28.

Other variations of construction may be used. For instance, coolant output port 28 may connect on the opposite side of gas trap 10 from its present position to either coolant exhaust chamber 26 or coolant chamber 20. Coolant exhaust chamber 26, while a convenient addition to gas trap 10, could also be eliminated leaving only coolant chamber 20.

In a preferred embodiment, thermocouple well 30 is disposed within coolant chamber 20. Thermocouple 32, in thermocouple well 30, allows monitoring of the temperature in coolant chamber 20. The measured temperature is closely associated with the temperature within gas column chamber 12. Other temperature monitoring devices could also be used. However, the thermocouple is suited for measuring wide swings in temperature ranging from approximately −200° C. to over 400° C.

Heating filament 34 is in surrounding relationship to coolant exhaust chamber 26. Heating filament 34 is housed, in a preferred embodiment, in coiled glass tubing 36. Coiled glass tubing 36 is also disposed in the annulus, or heating chamber, bounded by wall 40 which annulus surrounds coolant exhaust chamber 26. Coiled glass tubing 36 holds heating filament 34 in a fixed configuration. Fixing the configuration of heating filament 34 improves consistency of operation by preventing changes in heating characteristics that might otherwise occur over the passage of time. For instance, if heating filament 34 was allowed to sag or to bunch together, uneven heating and/or variable heating characteristics might result.

While heating filament 34 is disposed within the annulus formed by wall 40, heating filament 34 within coiled glass tubing 36 could conceivably be housed within exhaust coolant chamber 26, built into the walls of one of the annular components, or placed in other positions where it would be suitable for heating tubular column 14.

While the heating filament 34 is disposed within the annulus formed by wall 40, heating filament 34 within coiled glass tubing 36 could conceivably be housed within exhaust coolant chamber 26, built into the walls of one of the annular components, or placed in other positions where it would be suitable for heating tubular column 14.

While the heating filament 34 has a spiraling configuration in the presently preferred embodiment, it may take other configurations. For instance, the coils could be tightly packed at surrounding ends 16 and 18 of gas column chamber 12. This configuration compensates for heat lost at the end to provide more even heating of gas column chamber 12. The configuration could also include a plurality of surrounding filaments each running parallel to gas column chamber 12. Other configurations may also be used. A heating fluid pumped through heating coils or heat producing chemical reaction may also be used in place of or with heating filament 34.

Surrounding both heating filament 34 and coolant chamber 20 is Dewar flask Dewar flask 38 effectively insulates gas trap 10. Thus, heat flow to the atmosphere from gas trap 10 is limited. Heat from heating filament 34 for vaporizing liquified/solidified gas in gas column chamber 12 concentrates within Dewar flask 38 to allow fast vaporization. Fast vaporization is helpful for producing high resolution chromatograms.

Dewar flask 38 has double walls 40 and 42 with an evaluated annular volume 44 between the double walls. Vacuum may be drawn though evacuation ports 46 and 48 to evacuate annular volume 44 so it functions as an insulating space. After evacuation, ports 46 and 48 are sealed. Walls 40 and 42 are typically coated with heat reflective material. For instance, mirror silvering may be used to form heat reflective surfaces 50 and 52 respectively. The silvering process is typically completed before vacuum is drawn in annular column 44. Dewar flask 38 could also be formed in other shapes as desired and could include an evacuated portion on both sides of gas trap 10 along with the annular evacuated volume 44.

With Dewar flask 38 in place, input and output ports 22 and 24 could conceivably be closed (by means not shown), and gas trap 10 removed from the configuration with tubular column 14. The gas sample may stay in a liquid/solid state for a considerable amount of time due to the insulating effect of Dewar flask 38. It could then be placed in another desired configuration. The compact design of gas trap 10 allows considerable flexibility of use.

Most components of gas trap 10 are preferably made of glass-like material such as quartz. An additional outer housing (not shown) may surround gas trap 10 if desired. The components of gas trap 10 are typically fused together for sturdy one-piece or monolithic construction with walls on either side of gas trap 10 to which the internal, typically annular, components are physically connected and/or supported. Thus, five tubular members are shown which are fused on each side of walls. The gas trap 10 of the present invention may be in a compact form. For instance, in the present embodiment, the gas trap 10 has a length of approximately 150 mm. Thus, the present apparatus is convenient to use as well as being relatively simple to install and operate.

In operation, tubular column 14 is threaded through gas column chamber 12. Liquid nitrogen is introduced into coolant chamber 20 through input port 22 to liquify or solidify gas samples in gas column chamber 12. The gas sample is thereby effectively trapped in tubular column 14. Application of electric power to heating filament 34 vaporizes the liquified/solidified gas trapped in gas tubular column 14. The components of the gas with the lowest boiling points vaporize first. Fast vaporization will typically narrow the peaks of a subsequent chromatogram for improved resolution, if that is a desired result of the configuration used. Since the Dewar flask 38 limits power loss, ambient temperature conditions are not consequential.

Thus, the present invention allows for trapping gas samples in a compact manner convenient for most testing configuration.

The foregoing description of the invention has been directed in primary part to a particular preferred embodiment in accordance with the requirements of the patent statutes and for purposes of illustration. It will be apparent, however, to those skilled in the art that many modifications and changes may be made without departing from the scope and spirit of the invention. Therefore, the invention is not restricted to the preferred embodiment illustrated but covers all modifications which may fall in the scope of the following claims or the spirit of the invention.

We claim:

1. An apparatus for trapping a gas sample being carried through a tubular column comprising:
   means defining a gas column chamber into which at least a portion of said tubular column extends;
   means defining an annulus in surrounding relationship to said gas column chamber;
   means to introduce a coolant into said annulus;
   means for heating said gas column chamber in surrounding relationship to said gas column annulus.

2. The apparatus of claim 1 wherein said means to introduce a coolant into said annulus comprises a coolant input port and a coolant output port.

3. The apparatus of claim 1 further comprising insulating means in surrounding relationship to said means for heating said gas column chamber.

4. The apparatus of claim 3 wherein said insulating means comprises first and second walls defining an annular, insulating space between said walls.

5. The apparatus of claim 4 wherein said first wall is disposed in surrounding relationship to said second wall, said first and second walls having a heat reflective surface.

6. The apparatus of claim 4 including a heating chamber, said heating chamber being in surrounding relationship to said annulus, said means for heating said gas column chamber being disposed in said heating chamber.

7. The apparatus of claim 6, further comprising a coolant exhaust chamber in surrounding relationship to said annulus, said coolant exhaust chamber being in open communication with said annulus.

8. The apparatus of claim 7 wherein said gas column chamber, said annulus, said coolant exhaust chamber, said heating chamber and said insulating space are defined by a plurality of first, second, third, fourth and fifth tubular members disposed in consecutive, surrounding relationship to one another, the first of said tubular members being innermost, the fifth of said tubular members being outermost, each of said tubular members being adjoined on a first end to a first end wall and on a second end to a second end wall whereby said apparatus forms a monolithic structure.

9. The apparatus of claim 4 wherein said gas column chamber, said annulus and said insulating space are defined by a plurality of tubular members disposed in surrounding relationship to one another, each of said tubular members being adjoined on a first end to a first end wall and on a second end to a second end wall whereby said apparatus forms a monolithic structure.

* * * * *